United States Patent [19]

Jesson et al.

[11] 3,997,579
[45] Dec. 14, 1976

[54] SELECTED PHOSPHORUS COMPLEXES OF ZEROVALENT IRON

[75] Inventors: James Peter Jesson, Chadds Ford, Pa.; Chadwick Alma Tolman, Wilmington, Del.

[73] Assignee: E. I. Du Pont de Nemours and Company, Wilmington, Del.

[22] Filed: Oct. 15, 1975

[21] Appl. No.: 622,674

[52] U.S. Cl. .................. 260/439 R; 252/431 P; 260/465.3
[51] Int. Cl.² ................................. C07F 15/02
[58] Field of Search ................ 260/439 R

[56] References Cited
UNITED STATES PATENTS

| 3,450,732 | 6/1969 | Wilke et al. | 260/429 R |
| 3,903,120 | 9/1975 | Shook et al. | 260/439 R |

OTHER PUBLICATIONS

Malatesta et al. Ferovalent Compounds of Metals; Academic Press N.Y.; NY, 1904 p. 202–205.
Muerterties et al. J.C.S. Chem Comm. 1974 p. 850–851.
Meakin et al. J. Am. Chem. Soc. 97 (1975) p. 1254–1255.

*Primary Examiner*—Arthur P. Demers

[57] ABSTRACT

Selected novel phosphorus complexes of zerovalent iron containing phosphite ester ligands and, optionally diphosphine ligands, e.g., pentakis(trimethyl phosphite iron) and bis[ethylenebis(diphenylphosphine)] (trimethyl phosphite) iron, are disclosed. The compounds are prepared by various methods, by cocondensation of the vapors of iron and the ligand compound on a cold surface, e.g.,

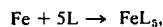

Fe + 5L → FeL₅, by displacement reaction of the ligand with bis(cyclooctadiene)iron, by "wet-reduction" methods (preferred), e.g.,

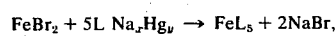

FeBr₂ + 5L Na$_x$Hg$_y$ → FeL₅ + 2NaBr, and, where two diphosphines are desired, by displacement of ethylenes, e.g.,

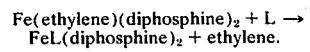

Fe(ethylene)(diphosphine)₂ + L →
FeL(diphosphine)₂ + ethylene.

The new compounds are useful as catalysts for the hydrocyanation of ethylene.

12 Claims, No Drawings

SELECTED PHOSPHORUS COMPLEXES OF ZEROVALENT IRON

BACKGROUND OF THE INVENTION

1. Field of the Invention

This invention relates to complexes of zerovalent iron containing phosphite ester ligands and, optionally, diphosphine ligands.

2. Prior Art

Zerovalent iron complexes containing unsaturated hydrocarbon ligands together with either phosphite-ester ligands or $PF_3$ ligands are known. In addition, pentakis(phosphorus trifluoride)iron, $Fe(PF_3)_5$, is a known compound. Zerovalent iron complexes containing diphosphine ligands in combination with other ligands such as ethylene are also known. No references other than 1 and 8, below, have been found to a zerovalent iron complex containing only phosphite-ester ligands or a combination of phosphite-ester ligands and diphosphine ligands. Other metals, particularly nickel, are known to form zerovalent complexes containing only phosphite-ester ligands.

Specifically:

1. Muetterties and Rathke, Chem. Commun., 850 (1974) disclose pentakis(trimethyl phosphite)iron(O), prepared by sodium-amalgam reduction of tris(trimethyl phosphite)-iron(II) chloride in the presence of excess of trimethyl phosphite. This is an example of a "wet-reduction" method.

2. Green and Whiteley, J. Chem. Soc. (A), 1943 (1971) disclose cyclopentadienetris(triphenyl phosphite)iron(O), made by a wet-reduction method.

3. British 979,778 (Shell, 1965) discloses tetrakis(bicycloheptadiene)(triphenyl phosphite)iron(O), also made by a wet-reduction method.

4. Timms, Advan. Inorg. Chem. Radiochem., 14 121–171 (1972), "Low Temperature Condensation of High Temperature Species as a Synthetic Method". This is a detailed review of the metal-atom-evaporation synthetic technique and a summary of the compounds that have been made by it.

5. Timms, Chem. Commun., 1033 (1969) discloses preparation of $Fe(PF_3)_5$, a known compound, by the metal-atom-evaporation method.

6. Warren et al., Inorg. Chem., 9, 373 (1970), and 11, 452 (1972), disclose 1,3-butadienetris(phosphorus trifluoride)iron(O) and 1,3-cyclohexadienetris(phosphorus trifluoride)iron(O).

7. Mackenzie and Timms, Chem. Commun., 650 (1974) disclose 1,5-cyclooctadienetris(phosphorus trifluoride)iron(O), made by metal-atom evaporation.

8. Meakin, English, Ittel, and Jesson, J. Am. Cham. Soc., 97, 1254 (1975; March 5) describe the nmr spectra of $FeL_5$ complexes in which L is trimethyl phosphite, triethyl phosphite, and tripropyl phosphite. The complexes were made by wet-reduction procedures.

SUMMARY AND DETAILS OF THE INVENTION

The products of the invention are compounds of the formula wherein:

the $R^1$'s are lower alkyl, chloro(lower alkyl), or oxa(lower alkyl) in which any chain branching or chloro substitution occurs at carbon removed from the oxygen by at least two other carbons, and may be the same or different;

$R^2$ is lower alkyl;

the $R^3$'s which may be the same or different, are primary or secondary lower alkyl, phenyl, 2-naphthyl, alkylphenyl of 7–10 carbons in which the alkyl group or groups are meta or para, phenylalkyl of 7–10 carbons in which the alkyl carbon bonded to phenyl bears at least one hydrogen, or alkylphenylalkyl of 8–10 carbons in which the carbon of the second-named alkyl moiety bonded to phenyl bears at least one hydrogen;

$n$ is 1, 2 or 3;

$a$ is 0–5;

$b$ is 0–5;

$c$ is 0, 1, or 2; and $a + b + 2c = 5$.

As noted, the $R^1$ groups, and also the $R^3$ groups, can be the same or different. Preferably, because of availability, the $R^1$ groups in any one $P(OR^1)_3$ ligand will be the same. Also preferably, and also because of availability, the two $R_2^3P$ moieties in a given diphosphine ligand will be the same, whether the two $R^3$ groups bonded to phosphorus are the same or different. Most preferably, all $R^3$ groups in a given diphosphine ligand will be the same. Preferably, one of $a$, $b$ and $c$ is 0.

Lower alkyl is defined as alkyl of up to 8 carbons. Examples are methyl, ethyl, isopropyl, t-butyl, neopentyl, hexyl, isoheptyl, 2-ethylhexyl, and octyl. A chloro(lower alkyl) group is a lower alkyl group containing one chloro substituent, e.g., 4-chlorobutyl. An oxa(lower alkyl) group is a lower alkyl group interrupted by an oxygen atom between two carbons. Such groups are also known as alkoxyalkyl groups. Examples are 3-oxabutyl (2-methoxyethyl), 6-oxaoctyl (5-ethoxypentyl), and 2-oxahexyl (butoxymethyl).

Examples of alkylphenyl, phenylalkyl, and alkylphenylalkyl groups are m- and p-tolyl, 3,4-xylyl, 3-ethylphenyl, 4-t-butylphenyl, benzyl, phenethyl, 4-phenylbutyl, p-tolylmethyl, and 3,5-dimethylphenethyl.

In all products of the invention the iron atoms are zerovalent, i.e., in an oxidation state of zero. Each phosphite-ester ligand present is bonded to iron through phosphorus. In products containing diphosphine ligands, each phosphorus atom of the diphosphine is bonded to the iron to form a chelate ring. Thus, in each product the iron is bonded to five phosphorus atoms.

The products of the invention can also be defned in terms of the cone angles of the individual phosphite ligands and the cone angles of the two phosphorus-containing moieties of each diphosphine ligand. Thus, the products can be defined as those of formula (A), wherein $R^1$ is lower alkyl, chloro(lower alkyl), or oxa(lower alkyl), the other terms are as defined previously, and the sum of the cone angles of all the phosphorus moieties bonded to iron is at most about 610°. Cone

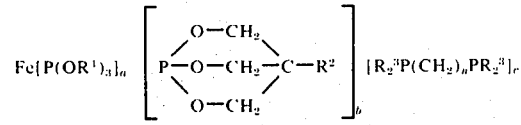

(A)

angles and the method for measuring them are discussed by Tolman in J. Am. Chem. Soc., 92, 2956 (1970) and J. Am. Chem. Soc., 96, 53 (1974). In any product of the present invention, five cone angles will be involved, corresponding to the five phosphorus atoms bonded to iron.

The products of the invention in which the ligands are all acyclic phosphites, bicyclic phosphites, or combinations of these types, i.e., compounds of formula (A) in which $c$ is 0, constitute a preferred group. These products are compounds of the formula

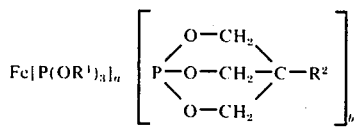  (B)

wherein:
R$^1$ and R$^2$ are as defined previously;
$a$ is 0–5;
$b$ is 0–5; and
$a + b = 5$.

When all five ligands in a product of formula (B) are the same, the cone angle of each ligand is at most about 116°, and preferably it is at most about 110°. These products constitute an especially preferred class.

The products of the invention, generically represented as FeL$_5$, where L represents a phosphite ligand or one-half a diphosphine ligand, can be made by several different methods.

1. When L is a relatively volatile phosphite ester, the products can be made by a metal-atom-evaporation process. This method, which is described in more detail below, involves cocondensation of the vapors of iron and the ligand compound L on a cold surface in a high vacuum. The reaction that takes place can be represented by the equation $$\text{Fe} + 5\text{L} \rightarrow \text{FeL}_5 \quad (1)$$

2. When the phosphite ligand L is a bicyclic ester of the type shown in formulas (A) and (B), which compounds have low vapor pressures and are hard to volatilize without decomposition, it can be advantageous to form the desired product by a displacement reaction. In this procedure, bis(cyclooctadiene)iron, Fe(COD)$_2$, a known compound, is reacted with the phosphite L:

$$\text{Fe(COD)}_2 + 5\text{L} \rightarrow \text{FeL}_5 + 2\text{COD} \quad (2)$$

A convenient way to carry out this overall process is to prepare bis(cyclooctadiene)iron by the metal-atom-evaporation technique and then allow it to react with the phosphite L in the same apparatus. The intermediate bis(cyclooctadiene)iron is kept below −30° C to keep it from decomposing.

3. The pentakis(trialkyl phosphite)iron products, FeL$_5$, can also be prepared by adaptations of known "wet-reduction" methods. Typically, an iron salt such as ferrous bromide is reacted with a reducing agent such as sodium amalgam in the presence of the trialkyl phosphite L:

$$\text{FeBr}_2 + 5\text{L} \xrightarrow{\text{Na}_x\text{Hg}_y} \text{FeL}_5 + 2\text{NaBr} \quad (3)$$

This is the preferred method for making these products.

4. Products containing two different types of phosphie ligands, FeL$_m$L'$_n$, where L and L' are different phosphite esters and $m + n = 5$, can be prepared by reacting a suitable iron source with a mixture of the two ligands L and L'. Either metal-atom-evaporation or wet reduction can be used. In the metal-atom-evaporation process, the reaction can be represented by the equation $$\text{Fe} + m\text{L} + n\text{L}' \rightarrow \text{FeL}_m\text{L}'_n \quad (4)$$

5. Products containing more than one type of phosphite ligand can also be prepared by displacing some of the L ligands in an FeL$_5$ product by reaction with an appropriate amount of L'. The equation for the reaction involved is $$\text{FeL}_5 + m\text{L}' \rightarrow \text{FeL}_{5-m}\text{L}'_m \quad (m = 1-4) \quad (5a)$$

The same technique can be used to prepare products containing three or one phosphite ligands, L, and one or two diphosphine ligands:

$$\text{FeL}_5 + n(\text{diphosphine}) \rightarrow \text{FeL}_{5-2n}(\text{diphosphine})_n + 2n\text{L} \quad (n = 1 \text{ or } 2) \quad (5b)$$

6. In addition, products containing both phosphite and diphosphine ligands can be prepared by replacement reactions of phosphite ligands, L, with known types of diphosphine-iron complexes, for example:

$$\text{Fe}(\text{C}_2\text{H}_4)[\text{Ph}_2\text{P}(\text{CH}_2)_n\text{PPh}_2]_2 + \text{L} \longrightarrow \quad (6)$$

$$\text{FeL}[\text{Ph}_2\text{P}(\text{CH}_2)_n\text{PPh}_2]_2 + \text{C}_2\text{H}_4$$

(Ph = phenyl)

$$\text{HFe}\begin{matrix}\text{C}_6\text{H}_4(\text{Ph})\text{P}(\text{CH}_2)_n\text{PPh}_2 \\ [\text{Ph}_2\text{P}(\text{CH}_2)_n\text{PPh}_2]\end{matrix} + (2m+1)\text{L} \longrightarrow \quad (7)$$

$$\text{FeL}_{2m+1}[\text{Ph}_2\text{P}(\text{CH}_2)_n\text{PPh}_2]_2{}_{-m} + m\text{Ph}_2\text{P}(\text{CH}_2)_n\text{PPh}_2$$

(m = 0 or 1; n = 1)

Diphosphine complexes of the types shown as reactants in equations (6) and (7) in which $n$ is 2 or 3 are described by Hata et al. in J. Amer. Chem. Soc., 90, 2278 (1968) and in U.S. Pat. No. 3,475,509 (1969). The corresponding complexes in which n is 1 can be prepared by using the appropriate methylenebis(diphosphines) in the procedures described by Hata et al.

The metal-atom-evaporation process mentioned above is one aspect of a recently developed technique that uses low-temperature condensation reactions of high-temperature species to carry out chemical syntheses. The technique is described in detail by Timms in Advan. Inorg. Chem. Radiochem., 14, 121–171 (1972). Briefly and generally, the metal to be reacted is vaporized under high vacuum, and the walls of the surrounding vacuum chamber are cooled with liquid nitrogen. This allows the vapor of a coreactant to be passed into the chamber while the metal is evaporating and then be condensed on the cold walls so rapidly that high-vacuum conditions are maintained. Even with substantial rates of addition of the coreactant, very little of it comes in contact with the hot metal source or reacts with the metal vapor species until the moment of condensation on the cold walls.

In the present preparations by this technique, iron is vaporized in a vacuum (usually between 0.01 $\mu$ and 1 $\mu$) from a crucible heated by passing an electric current (typically 60–100 amperes at 10–15 volts) through a molybdenum or tungsten wire coil, or by heating directly by an electron beam (typicaly 70–120 milliamperes at 10,000 volts). Apparatuses for vaporization by these two methods are shown on pages 132 and 136 of the Timms reference. Typical rates of vaporization are 0.1–2 g/hr, and preferably 0.5–1 g/hr. The phosphite or other ligand to be reacted with the iron is admitted to the high-vacuum chamber as a vapor from a magnetically stirred reservoir, at a rate such that the ligand:iron mole ratio is between about 5:1 and 25:1, preferably about 10:1. For ligands of relatively low volatility, the reservoir and transfer line can be heated to give higher vapor pressure and higher feed rates. The walls of the reaction chamber on which cocondensation of iron and ligand takes place are maintained at about −196° C with liquid nitrogen.

The following examples illustrate the products of the invention. All operations at or near atmospheric pressure were carried out under nitrogen.

EXAMPLE 1

Pentakis(trimethyl phosphite)iron $Fe[P(OCH_3)_3]_5$

The reactor was a glass resin-kettle type of vessel with a diameter of 4.5 in. and a depth of 7 in., whose design was essentially the same as that shown on page 132 of the Timms article. Iron pellets (3.641 g) were placed in an aluminum crucible protected by a molybdenum sheet-metal heat shield, and the vessel was cooled in liquid nitrogen. Under high vacuum, the temperature of the crucible and the iron was gradually increased by electrical heating until the cold glass wall began to darken from condensation of iron. Heating was continued at this power level while 9.95 ml of trimethyl phosphite was admitted as a vapor over a period of 50 minutes. Heating was stopped, the reaction chamber was shut off from the vacuum source, the liquid-nitrogen coolant was removed, and the reactor and contents were allowed to warm to room temperature over 15 hours. Unreacted trimethyl phosphite was evaporated under vacuum into a liquid-nitrogen trap. The black oily product mixture was blanketed with nitrogen for work-up. By weight difference, 0.575 g of iron was found to have been vaporized.

The product was extracted with four 5-ml portions of pentane, and the combined extracts were evaporated to constant weight to give 1.36 g of a brown oil. The $^{31}P$ nmr spectrum of a methanol solution of this product showed resonances below −160 ppm (relative to external 85% $H_3PO_4$), corresponding to coordinated $P(OCH_3)_3$ in $Fe[P(OCH_3)_3]_5$.

After evaporation of the methanol, the ir spectrum of the residual product on a mull plate was similar to that of the known compound $Ni[P(OCH_3)_3]_4$. The $^1H$ nmr spectrum in $C_6D_6$ showed a very strong broad resonance and $\tau 6.32$ (~ 15 Hz wide) [internal tetramethylsilane (TMS) was at $\tau$ 10.0] corresponding to the $OCH_3$ in $Fe[P(OCH_3)_3]_5$.

Additional product was obtained by extracting the material remaining after the initial pentane extraction with three 5-ml portions of methanol. A small amount of iron powder (0.025 g) was removed from the extract by fishing with a magnet. The methanol was evaporated, the residue was taken up in 6 ml of toluene, and the mixture was filtered. The $^{31}P$ nmr, ir, and $^1H$ nmr spectra of the material in solution in toluene were similar to those for the first part of the product described above.

EXAMPLE 2

Pentakis(trimethyl phosphite)iron $Fe[P(OCH_3)_3]_5$

In the apparatus of Example 1, 3.877 g of iron powder was charged to the crucible. By essentially the method of Example 1, the iron was heated and evaporated while 55.3 cc of trimethyl phosphite was admitted as a vapor over a period of 2 hours. After vacuum evaporation of excess trimethyl phosphite, the reactor was washed out with 60 cc of dioxane, and the resulting dark mixture was treated with 1 g of commercial filter aid and filtered. By weight difference, 0.68 g of iron was found to have been vaporized.

High-pressure liquid chromatography of a sample of the dioxane solution indicated that the product was a mixture, with major peaks at about 5.5 and 6.0 minutes. The latter peak indicated that presence of $Fe[P(OCH_3)_3]_5$; $Ni[P(OCH_3)_3]_4$, a known compound, gives a very strong peak also at 6.0 minutes under the same conditions. Another small sample of the dioxane solution was cooled in liquid nitrogen, the vessel was evacuated, 5 cc of carbon monoxide (measured at room temperature and pressure) was added, and the vessel was closed and allowed to warm to room temperature. High-pressure liquid chromatography of this mixture showed a new peak at 9.6 minutes, corresponding to the formation of $Fe[P(OCH_3)_3]_4(CO)$. The high-pressure liquid chromatography was carried out with 5-$\mu l$ injections of solution into a Du Pont model 830 liquid chromatograph with a 1-meter 2-mm ID column at ambient temperature, concave radiant elution (No. 5, 10%/min. at 500 psi) 2% p-dioxane/98% isooctane → 100% p-dioxane. The column was packed with solid glass cores with porous silica surfaces ("Corasil" II; Waters Associates).

EXAMPLE 3

Pentakis(triethyl phosphite)iron $Fe[P(OC_2H_5)_3]_5$

The apparatus was similar to that of Example 1, except that it was equipped for heating the crucible with an electron beam (cf. page 136 of the Timms article). The crucible was charged with an excess of a mixture of iron powder and iron wire. By essentially the method of Example 1, over a period of about 4.5 hours, 1.16 g of iron and 21.1 cc of triethyl phosphite were evaporated and cocondensed. During the evaporation the reservoir and the feeder tube for the triethyl phosphite were immersed in a vessel of water kept at about 24° C. The pressure in the reactor was about 0.05–0.15 $\mu$ during this time. The crucible was allowed to cool, the reactor was allowed to warm to room temperature, and excess triethyl phosphite was removed by pumping for 24 hours. The residual black oil was taken up in 20 cc of ethyl ether, and the mixture was filtered through alumina that had been saturated with ether. Vacuum evaporation of the filtrate to constant weight gave 5.1 g of dark, noncrystalline product.

Addition of carbon monoxide to a solution of a sample of the product in methylene chloride gave rise to absorption at 1850 cm$^{-1}$ in the infrared spectrum, corresponding to the formation of $Fe[P(OC_2H_5)_3]_4(CO)$ from $Fe[P(OC_2H_5)_3]_5$.

The $^1$H nmr absorption spectrum in $CDCl_3$ showed —$OCH_2CH_3$ as a broad complex band at $\tau$ 6.0 and —$OCH_2 \sim CH_3$ as a strong quintet at $\tau$ 8.71.

The $^{31}$P [$^1$H] absorption spectrum in pentane at 250° K showed an $A_2B_3$ multiplet pattern at $\sim$170 ppm, corresponding to $Fe[P(OC_2H_5)_3]_5$.

If trioctyl phosphite is substituted for triethyl phosphite in essentially the process of Example 3, pentakis(trioctyl phosphite)iron will be formed. If tris(2-methoxyethyl)phosphite is used, the product will be pentakis[tris(2-methoxyethyl) phosphite]iron. With tris(3-chloropropyl) phosphite, pentakis[tris(3-chloropropyl)phosphite]iron will be produced. In each of these preparations, it will be advantageous to warm the reservoir and feed tube for the phosphite ester appreciably above room temperature.

EXAMPLE 4

Pentakis(butylidynetrimethyl phosphite)iron

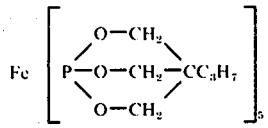

Bis(1,5-cyclooctadiene)iron, a known compound, was prepared in the apparatus of Example 1 by a modification of the method of Mackenzie and Timms, Chem. Commun., 650 (1974). A solution of about 0.2 mmol. of bis(1,5-cyclooctadiene)iron in 3 cc of tetrahydrofuran at ca. —40° C was added to 0.172 g (1 mmol.) of butylidynetrimethyl phosphite (systematic name 4-propyl-2,6,7-trioxa-1-phosphabicyclo[2.2.-2]octane) in a vessel chilled in solid carbon dioxide. The vessel was closed, shaken, and allowed to warm to room temperature with agitation. The $^{31}$P nmr absorption spectrum at —50° C showed a resonance of Fe[P-$(OCH_2)_3CC_3H_7$] at —160 ppm in addition to one of unreacted $P(OCH_2)_3CC_3H_7$ at —92 ppm.

EXAMPLE 5

Pentakis(propylidynetrimethyl phosphite)iron

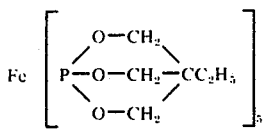

To a mixture of 12.80 g of anhydrous ferrous bromide and 500 ml of tetrahydrofuran was added 71.80 g of propylidynetrimethyl phosphite, and the mixture was cooled to —30° C. Sodium analgam was made from 3.50 g of sodium and 80 cc of mercury and added to the first mixture. The mixture was stirred for 7 hours at —20° C to —30° C, following which the supernatant liquid was decanted from the amalgam. It was stored in solid carbon dioxide overnight, following which volatile materials were evaporated under reduced pressure. The residual solvents were taken up in pentane, the mixture was filtered, and the filtrate was concentrated until crystals precipitated. The crystals were separated by filtration, the filtrate was again evaporated to dryness, and the residue was again taken up in pentane and the mixture was filtered. The filtrate was passed through neutral-grade alumina and evaporated once more to dryness. A pentane solution of the residual material was analyzed by $^{31}$P nmr and showed a peak at —161 ppm, corresponding to $Fe[P(OCH_2)_3CC_2H_5]_5$.

Substitution of triisopentyl phosphite for propylidynetrimethyl phosphite in the process of Example 5 will give pentakis(triisopentyl phosphite)iron as the product.

EXAMPLE 6

Pentakis(propylidynetrimethyl phosphite)iron

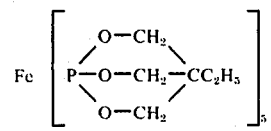

The chemistry involved in this example is the same as that in Example 4, but the technique involved is preferred over that of Example 4, in that decomposition of the intermediate iron-containing reactant is minimized by carrying the preparation of the final product in the same reactor used for the preparation of the intermediate.

In the bottom of the reactor of Example 1 was placed 15.8 g of propylidynetrimethyl phosphite, and bis(1,5-cyclooctadiene)iron was then prepared by cocondensation of 0.92 g of iron and 17 cc of 1,5-cyclooctadiene. At the end of the reaction, cooling of the walls of the reactor with liquid nitrogen was continued while the crucible was allowed to cool, following which about 50 cc of tetrahydrofuran was distilled into the reactor. Magnetic stirring of the propylidynetrimethyl phosphite in the bottom of the reactor was started, and the reactor was allowed to warm to room temperature. As the reactor walls warmed, the solid tetrahydrofuran that had condensed on the walls melted and dissolved the bis[1,5-cyclooctadiene)iron, and the solution ran down to the bottom of the reactor, where it reacted with the phosphite ester. The resulting solution was filtered through neutral-grade alumina, and the filtrate was evaporated under reduced pressure through constant weight to remove excess 1,5-cyclooctadiene. The product was dissolved in 100 cc of tetrahydrofuran, and the solution was treated with 50 cc of activated charcoal for 20 minutes and filtered. The resulting reddish-brown solution was passed through a column of neutral-grade alumina and evaporated to constant weight under reduced pressure, to give 9.69 g of yellow crystals that contained $Fe[P(OCH_2)_3CC_2H_5]_5$.

The room-temperature $^{31}$P nmr spectrum showed a line at —160.8 ppm corresponding to Fe[P-$(OCH_2)_3CC_2H_5]_5$, and also a line at —92.3 ppm corresponding to $P(OCH_2)_3CC_2H_5$. The proton nmr spectrum showed that the product was free of cyclooctadiene.

If octylidynetrimethyl phosphite is used in place of propylidynetrimethyl phosphite in essentially the procedure of Example 6, the product will be pentakis(octylidynetrimethyl phosphite)iron, $Fe[P(OCH_2)_3CC_7H_{15}]_5$.

EXAMPLE 7

Bis[ethylenebis(diphenylphosphine)](trimethyl phosphite)iron
$Fe[P(OCH_3)_3][(C_6H_5)_2PCH_2CH_2P(C_6H_5)_2]_2$ A mixture of 0.200 g of ethylenebis[ethylenebis(diphenylphosphine)]iron, 0.027 ml of trimethyl phosphite, and 2 cc of perdeuterotoluene was heated at 70° C for 1.5 hours. An additional 0.135 ml of trimethyl phosphite was added, and the mixture was heated at 70° C for 4 hours more. The $^{31}$P nmr spectrum of the solution showed new resonances at −155.2 and −87.2 ppm, corresponding to $Fe[P(OCH_3)_3][(C_6H_5)_2PCH_2CH_2P(C_6H_5)_2]_2$.

If ethylene[ethylenebis(dimethylphosphine]iron and ethylidynetrimethyl phosphite are used in essentially the procedure of Example 7, bis[ethylenebis(dimethylphosphine)]-(ethylidynetrimethyl phosphite)iron, $Fe[P(OCH_2)_3CCH_3][(CH_3)_2PCH_2CH_2P(CH_3)_2]_2$, will be formed. $Fe[P(OCH_3)_3]_3C_6H_5)_2PCH_2CH_2P(C_6H_5)_2$ can be made by reacting one mole of ethylenebis(diphenylphosphine) with pentakis(trimethyl phosphite)iron.

EXAMPLE 8

Bis(propylidynetrimethyl phosphite)tris(triethyl phosphite)iron and (propylidynetrimethyl phosphite)tetrakis(triethyl phosphite)iron

EXAMPLE 9

Pentakis(trimethyl phosphite)iron $Fe[P(OCH_3)_3]_5$

A solution of 0.83 g of ferrous bromide and 3.10 g of trimethyl phosphite in 60 ml of tetrahydrofuran was added slowly with stirring to an amalgam made from 0.1839 g of sodium and 2 cc of mercury, and the mixture overnight at room temperature. Volatile materials were removed under reduced pressure. The residual material was treated with warm pentane, a small amount of mercury was separated mechanically, and the mixture was filtered. The filtrate was concentrated to a volume of about 10 cc.

The room temperature $^{31}$P nmr spectrum of this solution exhibited one resonance at −180 ppm downfield from external 85% $H_3PO_4$, corresponding to $P(OCH_3)_3$ bonded to Fe through phosphorus. The spectrum at about −110° C showed a multiline pattern consistent with an $A_2B_3$ pattern, confirming the presence of five $P(OCH_3)_3$ ligands in the molecule.

EXAMPLE 10

Pentakis(trimethyl phosphite)iron $Fe[P(OCH_3)_3]_5$

A mixture of 12.80 g of anhydrous ferrous bromide, 55.0 g of trimethyl phosphite, and 500 ml of tetrahydrofuran was cooled to −30° C, and an amalgam made from 3.50 g of sodium and 80 cc of mercury was added with stirring. The mixture was stirred for seven hours at temperatures between −20° C and −30° C, and the liquid was decanted from the amalgam and cooled overnight in solid carbon dioxide. Volatile materials were evaporated under reduced pressure, the residual material was digested with pentane, the mixture was filtered, and the filtrate was evaporated to dryness. The residual material was dissolved in pentane and the solution was run through a column of neutral-grade alumina, following which the pentane was evaporated under reduced pressure to give yellow crystals of pentakis(trimethyl phosphite)iron.

Anal. Calc. for $C_{15}H_{15}FeO_{15}P_5$:
C, 26.65; H, 6.71; Fe, 8.26; O, 35.48; P, 22.90
Found: C, 27.0 ; H, 6.83; Fe, 10.05; O, 33.13; P, 24.33

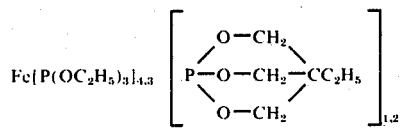

A solution of 0.11 g of pentakis(triethyl phosphite)iron and 0.097 g of propylidynetrimethyl phosphite in 1.7 cc of tetrahydrofuran was kept at room temperature for 5 days. After this time the $^{31}$P nmr spectrum showed new resonances corresponding to $Fe[P(OC_2H_5)_3]_4[P(OCH_2)_3C_2H_5]$ and $Fe[P(OC_2H_5)_3]_3[P(OCH_2)_3CC_2H_5]_2$.

By using larger amounts of propylidyne(trimethyl phosphite in the procedure of Example 8, $Fe[P(OC_2H_5)_3]_2[P(OCH_2)_3CC_2H_5]_3$ and $Fe[P(OCH_2H_5)_3][P(OCH_2)_3CC_2H_5]_4$ can be made.

EXAMPLE 11

Pentakis(triethyl phosphite)iron $Fe[P(OC_2H_5)_3]_5$

A mixture of 12.80 g of anhydrous ferrous bromide, 73.59 g of triethyl phosphite, 500 ml of tetrahydrofuran, and sodium amalgam made from 3.50 g of sodium and 80 cc of mercury was processed by essentially the method of Example 10. Following digestion with pentane and filtration, the filtrate was evaporated under reduced pressure to give an oil, which was redissolved in the minimum amount of pentane. Addition of acetone precipitated pale-green crystals of pentakis(triethyl phosphite)iron, which were separated by filtration and dried.

Anal. Calc. for $C_{30}H_{75}FeO_{15}P_5$:
C, 40.65; H, 8.53; O, 27.06; P, 17.47
Found: C, 39.1 ; H, 8.28; O, 30.0 ; P, 18.81.

The slight green color can be removed by treatment with alumina as described in Example 10.

EXAMPLE 12

Bis[ethylenebis(diphenylphosphine)](trimethyl phosphite)iron

Fe[P(OCH$_3$)$_3$][(C$_6$H$_5$)$_2$PCH$_2$CH$_2$P(C$_6$H$_5$)$_2$]$_2$

A solution of 2.56 g of HFe[C$_6$H$_4$(Ph)PCH$_2$Ch$_2$PPh$_2$][Ph$_2$PCH$_2$CH$_2$PPh$_2$] (Ph = phenyl) and excess trimethyl phosphite in toluene was stirred at room temperature for 24 hours. During this time Fe[P(OMe$_3$)][DPPE]$_2$ (P(OMe)$_3$ = trimethyl phosphite; DPPE = ethylenebis(diphenylphosphine)) precipitated as an orange-brown solid. About three-fourths of the liquid was evaporated under reduced pressure, and the product was separated by filtration, washed with ether and pentane, and dried. The $^{31}$P nmr spectrum of the product in perdeuterotoluene showed an AB$_4$ pattern, with a quintet in the phosphite region at −155.2 ppm downfield from external 85% phosphoric acid and a doublet in the phosphine region at −86.9 ppm; J ≅ 10 Hz. The product melted at 137°−138° C.

EXAMPLE 13

Bis[ethylenebis(diphenylphosphine)](propylidyne-trimethyl phosphite)iron

Fe[P(OCH$_2$)$_3$CC$_2$H$_5$][(C$_6$H$_5$)$_2$PCH$_2$CH$_2$P(C$_6$H$_5$)$_2$]$_2$

A solution of 2.58 g HFe[C$_6$H$_4$(Ph)PCH$_2$CH$_2$PPh$_2$][Ph$_2$PCH$_2$CH$_2$PPh$_2$] (Ph = phenyl) and 0.49 g of P(OCH$_2$)$_3$CC$_2$H$_5$ in toluene was stirred for 24 hours at room temperature. Part of the solvent was evaporated under reduced pressure and the mixture was cooled, whereupon Fe[P(OCH$_2$)$_3$CC$_2$H$_5$][DPPE]$_2$ precipitated as a microcrystalline orange-red powder, which was separated by filtration, washed with ether and pentane, and dried. The $^{31}$P nmr spectrum of the product in perdeuterotoluene showed an AB$_4$ pattern, with a quintet in the phosphite region at −140.6 ppm downfield from external 85% phosphoric acid and a doublet in the phosphine region at −90.5 ppm; J ≅ 8 Hz.

Anal. Calcd. for C$_{58}$H$_{59}$FeO$_3$P$_5$:
C, 68.65; H, 5.86; O, 4.73; P, 15.26
Found: C, 67.33; H, 6.17; O, 5.71; P, 15.09.

If HFe[CH$_3$C$_6$H$_3$(Tol)PCH$_2$CH$_2$CH$_2$Ptol$_2$]-[Tol$_2$PCH$_2$CH$_2$CH$_2$PTol$_2$] (CH$_3$C$_6$H$_3$ = 4-methyl-1,2-phenylene; Tol = p-tolyl) is used as the iron-containing starting material in essentially the procedure of the foregoing example, the product will be (propylidyne-trimethyl phosphite)bis[trimethylenebis(di-p-tolylphosphine)]iron.

EXAMPLE 14

[Methylenebis(diphenylphosphine)]tris(trimethyl phosphite)iron

Fe[P(OCH$_3$)$_3$]$_3$[C$_6$H$_5$)$_2$PCH$_2$P(C$_6$H$_5$)$_5$]

A solution of ethylenebis[methylenebis(diphenylphosphine)]iron and excess trimethyl phosphite in toluene was stirred for 24 hours at room temperature. Volatile materials were evaporated under reduced pressure, the residue was digested with pentane, and the mixture was filtered. The filtrate was evaporated under reduced pressure until an orange solid precipitated. The mixture was filtered, and the filtrate was evaporated to give a red oil. The presence of Fe[P(OMe$_3$)$_3$DPPM (DPPM = methylenebis(diphenylphosphine)) in the oil was shown by the $^{31}$P nmr spectrum (perdeuterotoluene), which showed an A$_3$B$_2$ pattern with a triplet in the phosphite region at −181.6 ppm downfield from external 85% phosphoric acid and a quartet in the phosphine region at −15.7 ppm; J ≅ 20 Hz.

If ethylenebis[methylenebis(dimethylphosphine)]iron is used as the iron-containing starting material in essentially the procedure of the foregoing example, [methylenebis(dimethylphosphine)]tris(trimethyl phosphite)iron will be produced.

EXAMPLE 15

Pentakis(tripropyl phosphite)iron

Fe[P(OC$_3$H$_7$)$_3$]$_5$

Anhydrous ferrous bromide (108 mg; 0.5 mmol) was dissolved in a solution of 552 μl of tripropyl phosphite and 10 ml of tetrahydrofuran. The solution was cooled to −25° C, and over a period of 10 minutes 3.5 ml of a solution of sodium napthalene (1.0 mmol) in tetrahydrofuran was added with stirring. The solution was stirred for one hour at room temperature. The residue was taken up in 3 ml of pentane, and the mixture was filtered through a glass wool and a Millipore filter into an nmr tube.

The $^{31}$P nmr spectrum obtained at −95° C showed an A$_2$B$_3$ spin system (J$_{AB}$ = 144 Hz; δ$_{AB}$ = 6.7 ppm), confirming the formation of pentakis(tripropyl phosphite)iron.

EXAMPLE 16

Bis[ethylenebis(diphenylphosphine)](tributyl phosphite)iron

Fe[P(OC$_4$H$_9$)$_3$][(C$_6$H$_5$)$_2$PCH$_2$CH$_2$P(C$_6$H$_5$)$_2$]$_2$

A solution of HFe[C$_6$H$_4$(Ph)PCH$_2$CH$_2$PPh$_2$][Ph$_2$PCH$_2$CH$_2$PPh$_2$] (Ph = phenyl) and excess tributyl phosphite in toluene was stirred at room temperature for 24 hours, and volatile materials were evaporated under reduced pressure. The residual solid was recrystallized from ether to give Fe[P(OBu)$_3$][DPPE]$_2$ (Bu=butyl) as a red crystalline solid, mp 134°−136° C.

Anal. Calcd for C$_{64}$H$_{75}$FeO$_3$P$_5$:
C, 69.7; H, 6.87; O, 4.4; P, 14.0
C, 68.6; H, 6.79; O, 5.1; P, 14.5.

The $^{31}$P nmr spectrum of the product in perdeuterotoluene showed an AB$_4$ pattern, with a quintet in the phosphite region at −156.0 ppm downfield from external 85% phosphoric acid and a doublet in the phosphine region at −86.3 ppm, J ≅ 11 Hz.

As shown in the following examples, the products of the invention are useful as catalysts for the hydrocyanation of ethylene.

EXAMPLE A

A solution of 0.034 g of pentakis (trimethyl phosphite) iron and 0.008 ml of hydrogen cyanide in 0.5 cc of tuluene was chilled in liquid nitrogen, and 5 cc of ethylene, measured at room temperature and pressure, was added. The vessel was closed, shaken, warmed to room temperature, and allowed to stand overnight. The infrared absorption spectrum of the solution now showed a band at 2253 cm$^{-1}$, characteristic of propionitrile. The assignment of this frequency was confirmed by gas chromatography and mass spectroscopy.

EXAMPLES B-D

The four compounds were pentakis(trimethyl phosphite)iron, pentakis(triethyl phosphite)iron Fe[P(OMe)$_3$][DPPE]$_2$ (Example 12), and Fe[P(OBu)$_3$][DPPE]$_2$ (Example 16). Each of four glass vessels was charged under nitrogen with 0.05 g of test compound, 0.5 cc of tetrahydrofuran, and 0.008 ml of hydrogen cyanide. The vessel was cooled in liquid nitrogen and evacuated, and 5 cc of gaseous ethylene was added. The vessel was closed and heated at 80° C for 24 hours, after which each mixture showed absorption in the infrared at 2243 cm$^{-1}$, characteristic of propionitrile dissolved in tetrahydrofuran.

We claim:
1. A compound of the formula

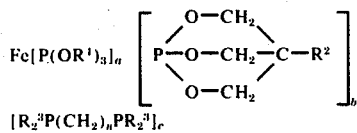

wherein:

the R$^1$'s are lower alkyl, chloro(lower alkyl), or oxa(lower alkyl) in which any chain branching or chloro substitution occurs at carbon removed from the oxygen by at least two other carbons, and may be the same or different;

R$^2$ is lower alkyl;

the R$^3$'s which may be the same or different, are primary or secondary lower alkyl, phenyl, 2-naphthyl, alkylphenyl of 7-10 carbons in which the alkyl group or groups are meta or para, phenylalkyl of 7-10 carbons in which the alkyl carbon bonded to phenyl bears at least one hydrogen, or alkylphenylalkyl of 8-10 carbons in which the carbon of the second-named alkyl moiety bonded to phenyl bears at least one hydrogen;

$n$ is 1, 2, or 3;

$a$ is 0–5;

$b$ is 0–5;

$c$ is 0, 1, or 2; and $a + b + 2c = 5$.

2. A compound of claim 1 wherein $c$ is o.

3. The compound of claim 1, pentakis(trimethyl phosphite)iron.

4. The compound of claim 1, pentakis(triethyl phosphite)iron.

5. The compound of claim 1, pentakis(butylidynetrimethyl phosphite)iron.

6. The compound of claim 1, pentakis(propylidynetrimethyl phosphite)iron.

7. The compound of claim 1, bis[ethylenebis(diphenylphosphine)](trimethyl phosphite)iron.

8. The compound of claim 1, bis(propylidynetrimethyl phosphite)tris(triethyl phosphite)iron.

9. The compound of claim 1, (propylidynetrimethyl phosphite)tetrakis(triethyl phosphite)iron.

10. The compound of claim 1, pentakis(tripropyl phosphite)iron.

11. The compound of claim 1, bis[ethylenebis(diphenylphosphine)](propylidynetrimethyl phosphite)iron.

12. The compound of claim 1, [methylenebis(diphenylphosphine)]tris(trimethyl phosphite)iron.

* * * * *

UNITED STATES PATENT OFFICE
CERTIFICATE OF CORRECTION

PATENT NO. : 3,997,579

DATED : December 14, 1976

INVENTOR(S) : James Peter Jesson and Chadwick Alma Tolman

It is certified that error appears in the above-identified patent and that said Letters Patent are hereby corrected as shown below:

Page 1, under OTHER PUBLICATIONS, "Ferovalent" should be --Zerovalent--.

Page 1, under ABSTRACT, second equation (Abstract, line 13), the arrow should be under "$Na_xHg_y$".

Column 2, line 53, "defned" should be --defined--.

Column 4, line 16, "phie" should be --phite--.

Column 4, in equation (5a) following line 30, "m = 1-4)" should be --(m = 1-4)--.

Column 4, in the second line of equation (7), the subscript "2 m" should be --2-m--.

Column 7, line 14, "$-OCH_2CH_3$" should be -- $-O\underline{C}H_2CH_3$ --.

Column 7, line 15, "$-OCH_2\sim CH_3$" should be -- $-OCH_2C\underline{H}_3$ --.

Column 10, line 8, before "overnight" insert --was stirred--.

Column 13, the formula in Claim 1 should be on one line as it appears at the bottom of Column 1.

Signed and Sealed this

Twelfth Day of April 1977

[SEAL]

Attest:

RUTH C. MASON  
Attesting Officer

C. MARSHALL DANN  
Commissioner of Patents and Trademarks